May 31, 1960 W. L. GORDON Plant Pat. 1,948
ROSE PLANT
Filed Dec. 19, 1958
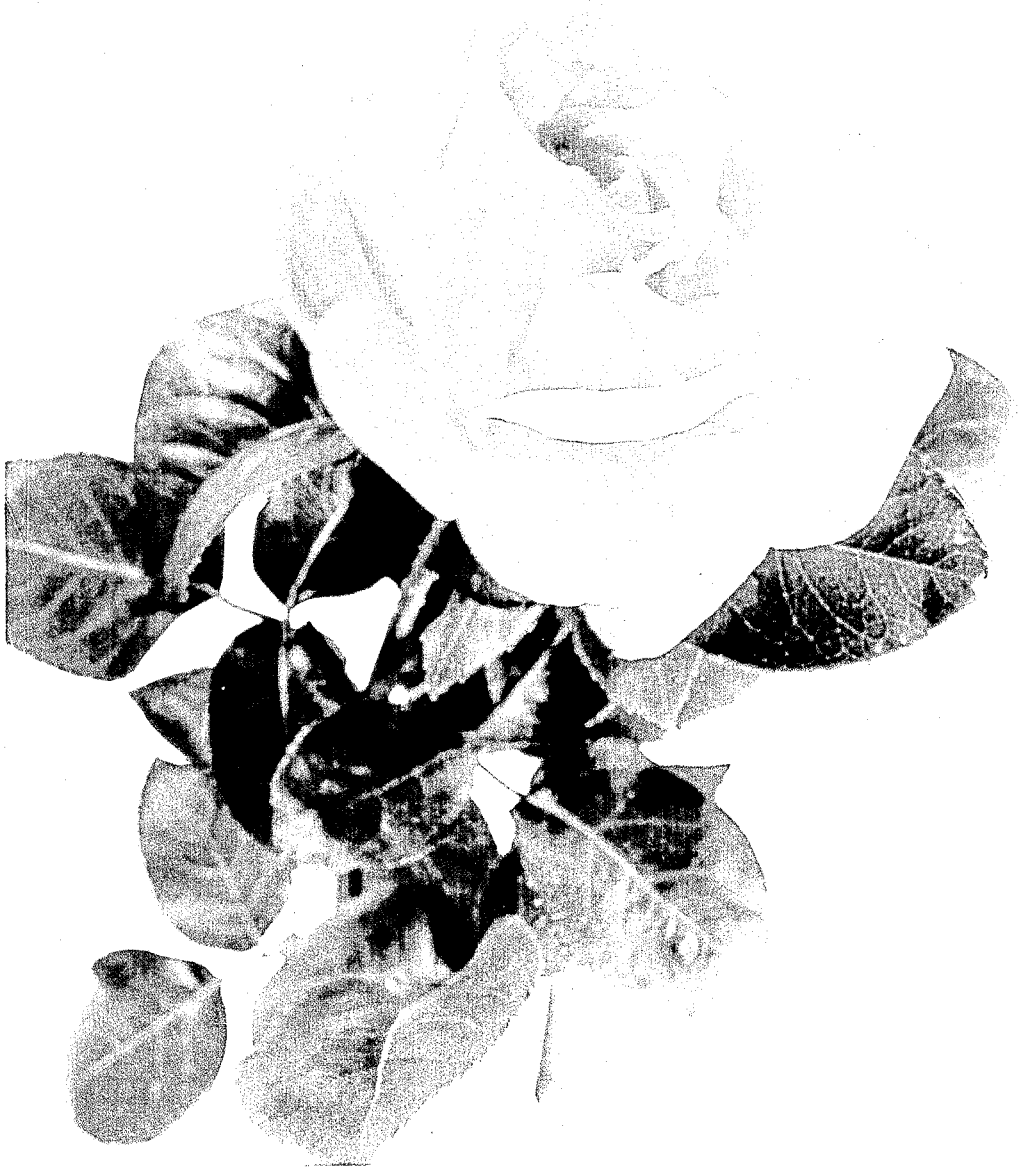
INVENTOR
WINIFRED L. GORDON
BY Robb & Robb
attorneys United States Patent Office Plant Pat. 1,948
Patented May 31, 1960

1,948

ROSE PLANT

Winifred L. Gordon, 6000 Chapel Road, North Madison, Ohio

Filed Dec. 19, 1958, Ser. No. 781,822

1 Claim. (Cl. 47—61)

The present invention relates to a new and distinct variety of rose plant of the hybrid tea class, which originated as a sport of the variety "Peace" (Plant Patent No. 591). The sport was found by me at North Madison, Ohio, among the cultivated plants of "Peace" which were growing in my garden. My attention was attracted to the bloom when it was first noticed because of the markedly different color thereof from the other blooms on the same plant and I thereupon carefully preserved the sport and promptly took steps to cause the same to be asexually reproduced in order to develop and ascertain whether the new color characteristic of the bloom was permanently established and transmissible by asexual reproduction.

Asexual reproduction of my new variety by cutting, grafting and budding, established that the new variety was not only distinguished from "Peace" by the orange-red general color tonality but I found it had other desirable characteristics which distinguish it from its parent, including certain distinguishing features such as the fewer number of petals which permit the general color tonality to be more prominent and the variegation in the color of the blooms from yellow to red.

The general color tonality distinguishes the rose plant of my invention from the variety "Peace" by reason of the fact that the "Peace" variety is substantially entirely yellow with only a tint of pink at the edges of the petals, the blooms gradually changing to white, further contrasting said blooms with those of my invention because the blooms of my invention do not turn white but become darker in general tonality as they mature.

Asexual reproduction of my new variety by cuttings, grafting and budding, as performed at Mentor, Ohio, shows that the foregoing characteristics and distinctions come true to form and are established and transmitted through succeeding propagations.

The accompanying drawing shows a specimen of the flower, foliage, and stems of my new variety.

The following is a detailed description of my new variety of rose plant, the color references being to the Flower Color Detector of the American Horticultural Council, except where general color terms of ordinary dictionary significance are applicable:

Parentage:

*Type.*—Hardy; sport; greenhouse and outdoor; for cut flowers and garden decorations.

*Class.*—Hybrid tea.

*Breeding.*—Sport of "Peace."

*Propagation.*—Holds its distinguishing characteristics through succeeding propagations by cutting, grafting and budding.

*Flower*

(Observations made from a plant grown outdoors in the month of August at North Madison, Ohio, U.S.A.)

Blooming habit: Intermittent.

Bud:

*Size.*—Very large.

*Form.*—Globular; wet weather does not affect it; not affected by hot weather.

*Sepals.*—Smooth edge; curl back soon after buds show color.

*Calyx.*—Funnel shaped. Size—broad. Aspect—smooth. Odor when rubbed—none.

*Peduncle.*—Length—medium. Aspect—prickly. Color—light green. Opening—bud opens well and is not affected by adverse weather conditions.

Bloom:

*Size.*—Very large; average size when fully expanded 5 to 6 inches.

*Borne.*—Several together.

*Stems.*—Long; strong.

*Form.*—When first opened—cupped. Permanence—retains its form to the end.

*Petalage.*—Double. Number of petals under normal conditions—45.

*Color.*—Center of flower—Light Orange, Plate 4. Outer petals—Strong Reddish Purple, Plate 2. Base of petals (singlet)—Strong Yellow, Plate 7. Inside of petals—Light Red, Plate 1. Reverse of petals—Very Pale Red, Plate 1. General tonality from a distance—Orange-Red, Plate 4.

*Variegations.*—Penciled and blotched.

*Discoloration.*—General tonality at end of first day—Reddish Orange, Plate 3. Second day—Light Orange-Red, Plate 2. Third day—Very Pale Orange-Red, Plate 2.

Petals:

*Texture.*—Thick, leathery, not affected by hot or wet weather.

*Appearance.*—Inside—satiny. Outside—satiny.

*Form.*—Scalloped.

*Arrangement.*—Imbricated (regularly arranged shingle-like).

*Petaloids in center.*—Few.

*Persistence.*—Hang on and dry.

*Fragrance.*—Moderate. Nature—tea (average hybrid scent).

*Lasting quality.*—On plant—long. As cut flower—long.

*Genital organs*

Stamens, anthers: Large.

*Color.*—Yellow.

*Arrangements.*—Regular around styles.

Stamens, filaments (threads): Medium.

*Color.*—Brown-red.

*Pollen.*—Gold-yellow.

*Styles.*—Even. Length—short.

*Stigmas.*—Color—yellow.

*Ovaries.*—Some protruding from calyx.

*Fruit*

Variety is sterile with its own pollen.

*Plant*

Form: Bush.

Growth: Very vigorous.

Foliage: 3 and 5 leaflets.

*Size.*—Large.

*Quantity.*—Normal

*Color.*—New foliage: upper side—bronzy; under side—reddish-bronze. Old foliage: upper side—normal green; under side—light green.

*Shape.*—Oval pointed.

*Texture.*—Upper side—leathery. Under side—smooth. Ribs and veins—ordinary.

*Edge.*—Serrated (saw-toothed).

*Serration.*—Single and small.

*Leaf stem.*—Color—green. Underside—prickles.

*Stipules.*—Long; bearded.

Wood:

*New wood.*—Color—light green. Bark—smooth.

*Old wood.*—Color—green. Bark—smooth.

Thorns:

*Thorns.*—Quantity—on main stalks—ordinary. Form—broad base; hooked downward. Color when young—green and red. Position—irregular.

*Prickles.*—Quantity: on main stalk—few; on laterals—few. Color—green.

*Short needles.*—Quantity: on main stalk—none; on laterals—none.

I claim:

A new and distinct variety of rose plant of the hybrid tea class, substantially as herein shown and described, characterized particularly as to novelty by its vigorous growing habit, by its full petalled flowers of orange-red general color tonality, by the variegation of the color of its blooms from yellow to red, by its very large blooms and its healthy, vigorous, and free blooming habit of growth.

No references cited.